United States Patent [19]

Sukigara et al.

[11] Patent Number: 5,587,358

[45] Date of Patent: Dec. 24, 1996

[54] POTENTIATORS OF ANTIMICROBIAL ACTIVITY

[75] Inventors: Masayuki Sukigara, Suzuka, Japan; Isao Kubo, Moraga, Calif.

[73] Assignee: Asahi Kasei Kogyo Kabushiki Kaisha, Osaka, Japan

[21] Appl. No.: 239,671

[22] Filed: May 9, 1994

[51] Int. Cl.$^6$ .................. A61K 38/12; A61K 31/11; A61K 31/405
[52] U.S. Cl. .................. 514/11; 514/415; 514/703
[58] Field of Search .................. 422/28, 36; 530/319; 514/9, 11, 415, 703, 159, 161, 210, 568, 724, 739, 164

[56] References Cited

U.S. PATENT DOCUMENTS

| | | | |
|---|---|---|---|
| 3,251,738 | 5/1966 | Scherr et al. | 514/11 |
| 4,225,585 | 9/1980 | Kida et al. | 424/114 |
| 5,380,763 | 1/1995 | Sato et al. | 514/724 |

FOREIGN PATENT DOCUMENTS

| | | |
|---|---|---|
| 0420630A2 | 4/1991 | European Pat. Off. . |
| 0420630A3 | 4/1991 | European Pat. Off. . |
| 1816451A1 | 5/1993 | U.S.S.R. . |

OTHER PUBLICATIONS

Journal of Natural Products vol. 57, No. 1, pp. 9–17, 1994.
J. Agric. Food Chem. 1993, 41, 1106–1109.
Journal of Natural Products vol. 57, No. 5, pp. 654–657, 1994.
Demain et al, "Antibiotics Containing the Beta–Lactam Structure", Part I, Published 1983 by Springer–Verlag (NY), p. 21).
J. Antibiotics, vol. 33, No. 6, issued Jun. 1980, "Penicillin–Binding Protiens in Bacillus Subtilis . . . ", pp. 614–619.
J. Agric. Food Chem., vol. 41, No. 6, issued Jun. 1993, Kubo et al, "Structure–Antibacterial Activity . . .", pp. 1016–1019.
J. Agric. Food Chem., vol. 41, No. 12, issued 1993, Kubo et al, "Antibacterial Activity of Long–Chain Alcohols . . .", pp. 2447–2450.
J. Food Science, vol. 58, No. 4, issued 1993, Vaughn et al, "Volatile Compunds from Raspberry and Strawberry . . .", pp. 793–796.
Muroi et al., 1993, "Bactericidal Activity of Anacardic Acids against *Streptococcus mutans* and Their Potentiation", *J. Agric. Food Chem.* 41:1780–1783.
Himejima et al., 1991, "Antibacterial Agents from the Cashew *Anacarduim occidentale* (*Anacardiaceae*)Nut Shell Oil", *J. Agric Food Chem.* 39:418–421.
Kubo et al., 1987, "Prostaglandin Synthetase Inhibitors from the African Medicinal Plant *Ozoroa mucronata*", *Chemistry Letters*, pp. 1101–1104.
Kubo et al., Oct., 1992, "Antibacterial Activity of Totarol and its Potentiation", *J. of Natural Products* 55(10):1436–1440.
Kubo et al., 1993, "Antitumor Agents from the Cashew (*Anacarduim occidentale*) Apple Juice", *J. Agric. Food Chem.* 41:1012–1015.
Kubo et al., 1986, "Molluscicides from the Cashew *Anacarduim occidentale* and Their Large–Scale Isolation", *J. of Agric. Food Chem.* 34:970–973.
Kubo et al., "Antibacterial Activity of Long–Chain Alcohols against *Streptococcus mutans*", *Advance ACS Abstracts*, Oct.15, 1993.
Bhattacharya et al., 1987, "Pharmacological Investigation on Soduim Salt and Acetyl Derivative of Anacardic Acid", *Phytotherapy Research* 1(3):127–134.

*Primary Examiner*—Jeffrey E. Russel
*Attorney, Agent, or Firm*—Pennie & Edmonds

[57] ABSTRACT

The present invention provides antimicrobial compositions, especially compositions comprising an antimicrobial (microbiocidal or microbiostatic) compound and a potentiator of antimicrobial activity. Compositions of the invention combining an antimicrobial compound and a potentiator are able to kill or inhibit the growth of microorganisms using much lower concentrations of the antimicrobial compound. The potentiator also enhances the efficacy of antimicrobial compounds against resistant strains of the microorganism.

11 Claims, No Drawings

POTENTIATORS OF ANTIMICROBIAL ACTIVITY

FIELD OF THE INVENTION

The invention pertains to antimicrobial compositions, in particular to compositions comprising a microbiocidal or microbiostatic compound and a potentiator of antimicrobial activity.

BACKGROUND

The development of antibiotic resistance has become a serious problem in medical microbiology. Newer generation β-lactam antibiotics such as methicillin were developed largely to overcome the resistance to earlier developed types of penicillins; such resistance has spread rapidly among pathogenic bacteria. However, methicillin resistant bacterial strains are now frequently encountered, notably among the *Staphylococci*.

Non-β-lactam antibiotics are often used for treating particular types of infection. Polymyxins are often used for treating skin infections due to gram-negative bacteria, such as Pseudomonas. However, the toxicity of these compounds restricts their parenteral use, and these compounds usually are administered topically in ointments. Polymyxins are not known to be effective against microorganisms other than gram-negative bacteria.

Fungal infections generally are treated with quite different types of antibiotics. Notably, topical Candida infections usually are treated with imidazole derivatives (e.g., clotrimazole) or nystatin.

SUMMARY OF THE INVENTION

The present invention provides antimicrobial compositions, especially compositions comprising an antimicrobial (microbiocidal or microbiostatic) compound and a potentiator of antimicrobial activity. Compositions of the invention combining an antimicrobial compound and a potentiator are able to kill or inhibit the growth of microorganisms using much lower concentrations of the antimicrobial compound. The potentiator also enhances the efficacy of antimicrobial compounds against resistant strains of the microorganism.

Exemplary compositions of the invention comprise a β-lactam antibiotic such as methicillin, or a C11–C15 long chain saturated or unsaturated aliphatic alcohol antibiotic, and an anacardic acid potentiator. Such compositions are effective against bacteria such as methicillin resistant *Staphylococcus aureus* (MRSA).

Other exemplary compositions comprise a polymyxin antibiotic and an indole or 2-hexenal potentiator. Such compositions are effective against both gram-negative and gram-positive bacteria, and also against fungi such as yeasts.

The invention also provides methods for inhibiting the growth of microorganisms by contacting the microorganism with a compound of the invention.

The antibiotic component of the composition may be a β-lactam, a polymyxin, or a long chain (C11, C12, C13, C14, or C15) aliphatic alcohol; the alcohol may be saturated or unsaturated, branched or linear. The potentiator of antibiotic activity may be an anacardic acid, indole or 3-alkyl indole, or an alkenyl aldehyde. The potentiators by themselves usually exhibit weak antibiotic activity. However, the combination compositions have synergistic antibiotic activities which enable use of reduced amounts of the antibiotic component.

Compositions comprising an antibiotic component and a potentiator may be used to treat in vivo infections, or to disinfect topical surfaces such as bandages, bodily appliances, catheters, surgical instruments, patient examination tables, etc.

For treatment of in vivo infections, the compositions may be administered either internally or externally. For external administration, the compositions may be used to treat infections of the skin or mucosal surfaces, infected cuts, burns, or abrasions, bacterial skin infections, or fungal infections (e.g., athlete's foot). For internal administration, the compositions are useful for treating systemic bacterial infections, especially Staphylococcus infections. Other compositions may be administered internally by topical administration to mucosal surfaces, such as vaginal mucosa, for treatment of infections, particularly yeast infection.

Compositions for in vivo administration may be provided as solutions, especially aqueous solutions, but optionally may include alcoholic solutions to increase the solubility of hydrophobic components. Such solutions are convenient for oral administration but may be formulated for parenteral administration. For oral administration, ethanol is preferred because of its low toxicity. Usually ethanol will be present in the minimum concentration needed to keep the components in solution. For external topical application, isopropanol may be used also. Other formulations for oral administration may include solid dosage forms such as tablets or capsules. Compositions preferred for topical administration may be provided as emulsions, creams, or liposome dispersions, or as an ointment in a hydrophobic carrier such as petrolatum.

For topical disinfection of nonliving surfaces, compositions may be provided as solutions, either aqueous or organic. Where direct human contact with the disinfectant is to be limited, such as in disinfection of work surfaces or restrooms, mixed organic solutions may be appropriate, e.g., ethanol or isopropanol in water. Preferred alcohols for solvent purposes include ethyl, n-propyl, isopropyl, n-butyl, isobutyl, and t-butyl alcohols. Concentration of the alcohol in a mixed solvent system may range from 5% to essentially 100%. Usually the cosolvent will be water or an aqueous buffer. In most cases, the alcohol component will be limited to an amount necessary to keep the antibiotic and potentiator in solution.

DETAILED DESCRIPTION OF THE INVENTION

The present invention provides pharmaceutical compositions comprising an antibiotic and a potentiator of antibiotic activity. Compositions of the invention are useful in suppressing the growth or infectivity of microorganisms which are resistant to the antibiotic in the absence of potentiators. The antibiotic component of the compositions may be a β-lactam antibiotic, a polymyxin, or a long chain (C11, C12, C13, C14, or C15) saturated or unsaturated, linear or branched aliphatic alcohol. The potentiator of antibiotic activity may be an anacardic acid, indole or a 3-alkyl indole, or an alkenyl aldehyde such as 2-hexenal.

The invention also provides methods of inhibiting the growth of microorganisms by contacting the microorganisms with compositions of the invention. These methods are effective against infections in vivo. This is demonstrated by test data showing the minimum inhibitory concentrations (MIC) and minimum biocidal concentrations (MBC) of compositions against various pathogenic organisms cultured in vitro under standard conditions. These in vitro tests strongly correlate with in vivo activity, as is evidenced by the widespread use of the MIC and MBC determinations to predict utility of antimicrobial compositions in treatment of infection in animals, including humans. The methods of the invention also disinfect external surfaces, including intact skin, countertops, medical instruments, bandages and wound dressings, and the like.

Particularly striking is the ability of the present compositions, comprising a potentiator and an antimicrobial compound, to extend the range of antimicrobial effectiveness against microorganisms previously considered unreactive towards the antimicrobial compound. For example, antibiotic activities of polymyxins have been considered to be restricted to gram-negative bacteria such as *E. coli* and *Pseudomonas aeruginosa*. However, compositions of the invention extend the antimicrobial effect of polymyxins to gram-positive bacteria such as *Staphylococcus aureas*, and to fungi, including yeasts such as *Candida albicans*.

A particular advantage of these compositions is their reduced toxicity. Because of the synergy between the antibiotic and potentiator components, the amount of antibiotic required is reduced. Since the antibiotics are toxic both to humans and the environment, the reduced use of antibiotics is highly desirable.

In addition, the potentiators are relatively less toxic than conventional antibiotics; many of them, such as anacardic acid, indole, farnesol, and 2-hexenal, occur naturally in foods and are routinely consumed in the diet without apparent harm. Therefore pharmaceutical compositions comprising these potentiators are expected to have low toxicity as well.

4.1 Formulations

Compositions of the invention may be provided as topical disinfectants for sterilization of surfaces such as countertops, surgical instruments, bandages, and skin; as pharmaceutical compositions, including by way of example creams, lotions, ointments, or solutions for external application to skin and mucosal surfaces, including the cornea, dermal cuts and abrasions, burns, and sites of bacterial or fungal infection; as pharmaceutical compositions, including by way of example creams, lotions, ointments, emulsions, liposome dispersions, tablets, or solutions, for administration to internal mucosal surfaces such as the oral cavity or vagina to inhibit the growth of bacteria or fungi, including yeasts; and as pharmaceutical compositions such as creams, gels, or ointments for coating indwelling catheters and similar implants which are susceptible to harboring bacterial or fungal infection.

Anacardic acid, C11–C15 long chain aliphatic alcohols, and polymyxins have limited solubilities in aqueous solution. Compositions comprising any of these compounds optionally may be formulated with a lipophilic phase, as in emulsions and liposome dispersions.

For external application to intact skin or for disinfection of nonliving surfaces, an organic solvent or cosolvent such as ethanol or propanol may be employed. Evaporation of the solvent leaves a residue of the antibiotic and potentiator on the treated surface to inhibit reinfection.

Although the potentiator components frequently occur as components in food, for most uses a food or unpurified plant source does not adequately substitute for a partially or even highly purified potentiator in formulations of the invention. The additional components present in plant sources often contain undesirable components as well as the potentiator.

For example, most food or plant sources of anacardic acid (i.e., cashew apple), farnesol (i.e., lemon grass), or 2-hexenal (i.e., fruits, green leaves) also contain compounds such as sugars which support the growth of microorganisms. These are undesirable in vaginal or skin ointments or in topical disinfectants. Preferred compositions of the invention, especially topical compositions, may be substantially free of sugars in amounts which support the growth of microorganisms.

Particular formulations may be manufactured according to methods well known in the art. Formulations are given in, for example, *Remington's Pharmaceutical Sciences* and similar reference works.

4.2. Anacardic Acid

A preferred potentiator of antimicrobial activity is anacardic acid. As used herein, the term "anacardic acid" refers to a 2-hydroxy-6-R-benzoic acid,

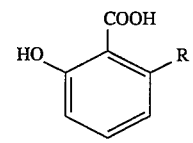

wherein R is an alkyl or alkenyl chain of 10 to 15 carbon atoms. Anacardic acids of particular interest include those wherein R is the 8(Z),-11(Z),-14-pentadecatrienyl chain; the 8(Z),-11(Z)-pentadecyldienyl chain; the 8(Z)-pentadecylenyl chain; the dodecyl chain; or the decyl chain. These compounds may be denoted respectively the (15:3), (15:2), (15:1), (12:0), and (10:0) anacardic acids:

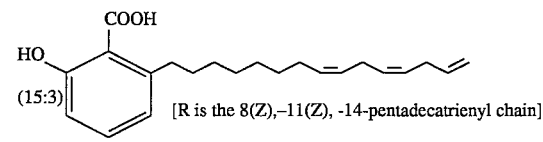

[R is the 8(Z),-11(Z), -14-pentadecatrienyl chain]

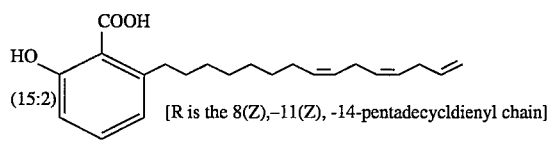

[R is the 8(Z),-11(Z), -14-pentadecycldienyl chain]

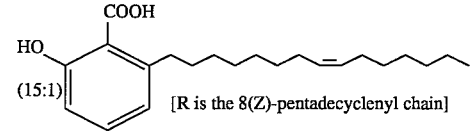

[R is the 8(Z)-pentadecyclenyl chain]

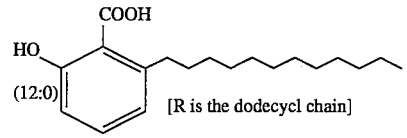

[R is the dodecycl chain]

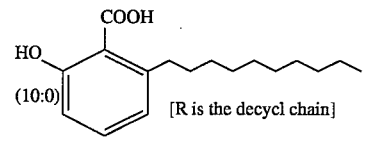

[R is the decycl chain]

The natural anacardic acids (15:3), (15:2), and (15:1) may be obtained conveniently by isolation from the nut shell oil of the cashew, *Anacardium occidentale* L. (Anacardiaceae). Purification may be effected by medium pressure liquid chromatography, as previously described (Kubo et al., *J. Agric. Food Chem.* (1986) 34: 970–973; Bagchi et al., *Planta Med.* (1985) 467); further purification may be performed by HPLC (Kubo et al., *Chem, Letters* (1987) 1101–1104; Kubo and Nakatsu, LC-GC (1991) 8: 933–939). The nonnatural C10 and C12 analogues may be synthesized as described (Kubo et al., *J. Agric. Food Chem.* (1993) 41:1016–1019).

Anacardic acid is particularly effective in combination with a β-lactam antibiotic such as methicillin, or in combination with bacteriocidal C11, C12, or C13 n-alcohols, to generate compositions inhibiting methicillin-resistant *Staphylococcus aureus*.

Compositions comprising a β-lactam antibiotic and an anacardic acid in a parenterally acceptable pharmaceutical vehicle are provided for parenteral administration. This route of administration is preferred because of the instability of many β-lactam antibiotics, including methicillin, in the acidic stomach environment, a circumstance which precludes effective oral administration. Because of the limited solubility of anacardic acids in water or aqueous solution, parenteral formulations may include emulsions or liposome dispersions. Alternatively, the anacardic acid may be converted to the more water-soluble sodium salt for administration in aqueous solution.

4.3 C11–C15 Aliphatic Alcohols

Aliphatic alcohols have moderate to weak antibiotic activity by themselves, and may be combined with a potentiator in compositions of the invention. Preferred compositions comprise aliphatic alcohols, especially n-alcohols and 2-alkanols having 11 to 13 carbons between the hydroxyl group and the end of the aliphatic chain, and an anacardic acid potentiator.

Preferred aliphatic alcohols include n-undecanol, n-dodecanol, n-tridecanol, 2-dodecanol, 2-tridecanol, 2-tetradecanol, and farnesol.

Emulsions and liposomes are useful in formulations comprising anacardic acid and an antibiotic C11–C15 aliphatic alcohol. In these compositions, both the antibiotic alcohol and the anacardic acid potentiator have low solubility in aqueous solutions.

These compositions are effective against gram-positive bacteria, including *S. aureus*, and particularly including methicillin resistant strains.

4.4 Indole and 2-Hexenal Potentiators

Indole and 3-substituted indoles are effective potentiators in combination with a polymyxin antibiotic. Active indole derivatives include 3-alkyl indoles, especially the 3-methyl (skatole) or 3-ethyl derivatives, and also the 3-carboxylic derivative. The N-H ring group preferably is left intact.

Trans-2-hexenal is also an effective enhancer.

5. Experimental Procedures 5.1 Test Microorganisms

Microorganisms were strains supplied by the ATCC. *Staphylococcus aureus* is a clinically significant member of the gram-positive group of bacterial pathogens. It gives rise to serious infections, and may produce bacteremia, endocarditis, and meningitis. Methicillin-resistant strains of *Staphylococcus aureus* were chosen for evaluation because they are a significant medical problem, in view of the fact that methicillin is the drug of choice for treatment of *S. aureus* infection in the common penicillin-resistant strains.

*Pseudomonas aeruginosa* was also chosen for evaluation. *P. aeruginosa* is a gram-negative pathogenic bacillus which may cause urinary tract infections or pneumonia.

*Candida albicans* is a eukaryotic fungus rather than a bacterium, and consequently would be expected to exhibit very different antibiotic susceptibilities from bacteria. In particular, *C. albicans* is a yeast, and is responsible for vaginal and oral thrush, and for skin and lung infections.

5.2 Methods of Testing 5.2.1 MIC Determination

The MICs were determined by the broth dilution method. Test compounds were dissolved in DMF (except methicillin, which was dissolved in sterile distilled water) to make stock solution at concentrations of 80, 40, 20, or 10 mg/ml depending upon the potency and solubility. An aliquot of 0.01 ml of the stock solution was added to a tube containing 0.99 ml of media to get the initial concentration of testing solution. Serial two-fold dilutions were made by mixing 0.5 ml of testing solution with 0.5 ml of blank medium. A 0.5 ml aliquot of diluted inoculum containing an appropriate concentration of the test microorganism (1:100 dilution of the initial inoculum) was then added into each tube containing 0.5 ml serial dilutions of the test compound. After incubating for 2 days at 37° C., the tube was evaluated for visible growth. The MIC was determined as the lowest concentration of a compound which prevented visible microorganism growth. A culture growth control without compound (solvent only) and several culture sensitive reference agents were used as positive controls. The assays were performed in duplicate.

5.2.2 MBC Determination

After determining the MIC, 0.1 ml of a ten-fold dilution from each tube showing no turbidity was plated onto chemical free nutrient agar plates. After 24 hours of incubation, the colonies were counted. The MBC was the lowest concentration of antibacterial compound that decreased the initial inoculum popoulation by >99.9 percent. The initial population for *E. coli.* was $1 \times 10^7 – 6 \times 10^7$ colony forming units (CFU) per ml; for *P. aeruginosa* was $1 \times 10^6 – 5 \times 10^6$ CFU per ml; and for methicillin-resistant *Staphylococcus aureus* (MRSA) was $2 \times 10^6 – 7 \times 10^6$ CFU per ml.

5.2.3 Synergic Effect Studies

Synergic effects of a putative potentiating substance in combination with an antibiotic reference compound were evaluated by a broth checkerboard method. Serial two-fold dilutions of the antibiotic reference compound in combination with a concentration of ½ MIC of the putative potentiating substance were made by the above described tube dilution method for determination of MICs and MBCs in each testing strain.

Since the potentiator is present at ½ of its MIC, the MIC determined for the antibiotic should be ½ of its usual value, if the effects of the two compounds are merely additive; greater than ½, if the compounds are antagonistic; and less than ½, if the compounds are synergistic. The "synergic effect" shown in the following Tables is the ratio of the MIC for the antibiotic alone to the MIC for the antibiotic in the presence of ½ MIC of the potentiator. A 2× synergic effect means that the activities of the antibiotic and potentiator are merely additive, whereas an effect greater than 2× indicates the occurrence of true synergy.

6. Example: Synergic Effect of Anacardic Acids with Methicillin on *Staphylococcus aureus*

Tests were performed to determine the synergic effect of anacardic acids with methicillin on methicillin-resistant *Staphylococcus aureus* (ATCC 33591). Results are given in Table 1.

TABLE 1

| Testing Strain | MIC (μg/ml) | | | Synergic Effect |
|---|---|---|---|---|
| | Methicillin Alone | Anacardic Acid Alone | Anacardic Acid (½ MIC) +Methicillin | |
| Methicillin-resistant Staphylococcus aureus (ATCC 33591) | 800 | 6.25 | 25 | 32x |

7. Example: Polymyxin Antibiotics and Indole or t-2-Hexenal Potentiators

Polymyxin antibiotics are known to be restricted in activity to gram-negative bacteria such as E. coli and Pseudomonas aeruginosa. As a result of incorporation of indole or t-2-hexenal potentiators into compositions of the invention, the range of activity of polymyxins is remarkably extended to include not only gram-positive bacteria such as Staphylococcus aureus, but even fungi as well. Notably, compositions comprising a polymyxin and indole are effective against yeast, including Candida.

7.1 Synergic Effects of Indole or t-2-Hexenal with Polymyxin B on Gram-negative Bacteria Tests were performed to determine the synergic effect of indole or t-2-hexenal with polymyxin B on gram-negative bacteria of the strains *Escherichia coli* (ATCC 10536) and *Pseudomonas aeruginosa* (ATCC 10145). Results are given in Table 2.

TABLE 2

| Testing Strain | MIC and MBC (μg/ml) | | | | | | | | Synergic Effect | |
|---|---|---|---|---|---|---|---|---|---|---|
| | Polymyxin B Alone | | Indole Alone | | Indole (½ MIC) +Polymyxin B | | | | | |
| | MIC | MBC | MIC | MBC | MIC | MBC | MIC | MBC | | |
| *Escherichia coli* (ATCC 10536) | 3.13 | 3.13 | 800 | 800 | 0.20 | 0.39 | 16X | 8X | | |

| Testing Strain | MIC and MBC (μg/ml) | | | | | | | | Synergic Effect | |
|---|---|---|---|---|---|---|---|---|---|---|
| | Polymyxin B Alone | | t-2-Hexenal Alone | | t-2-Hexenal (½ MIC) +Polymyxin B | | | | | |
| | MIC | MBC | MIC | MBC | MIC | MBC | MIC | MBC | | |
| *Escherichia coli* (ATCC 10536) | 3.13 | 3.13 | 400 | 400 | 0.39 | 0.39 | 8x | 8x | | |

| | Polymyxin B Alone | | Indole Alone | | Indole (½ MIC) +Polymyxin B | | | | | |
|---|---|---|---|---|---|---|---|---|---|---|
| | MIC | MBC | MIC | MBC | MIC | MBC | MIC | MBC | | |
| *Pseudomonas aeruginosa* (ATCC 10536) | 6.25 | 6.25 | 400 | 800 | 0.39 | 0.78 | 16x | 8x | | |

| Testing Strain | MIC and MBC (μg/ml) | | | | | | | | Synergic Effect | |
|---|---|---|---|---|---|---|---|---|---|---|
| | Polymyxin B Alone | | t-2-Hexenal Alone | | t-2-Hexenal (½ MIC) +Polymyxin B | | | | | |
| | MIC | MBC | MIC | MBC | MIC | MBC | MIC | MBC | | |
| *Pseudomonas aeruginosa* (ATCC 10536) | 6.25 | 6.25 | 200 | 400 | 0.78 | 0.78 | 8x | 8x | | |

7.2 Synergic Effect of Indole or t-2-Hexenal with Polymyxin B on Gram-Positive Bacteria Tests were performed to determine the synergic effect of indole or t-2-hexenal with polymyxin B on gram-positive bacteria on a methicillin and polymyxin B-resistant strain of *Staphylococcus aureus* (ATCC 33591). Results are given in Table 3.

TABLE 3

| Testing Strain | MIC and MBC (μg/ml) | | | | | | Synergic Effect | |
|---|---|---|---|---|---|---|---|---|
| | Polymyxin B Alone | | Indole Alone | | Indole (½ MIC) +Polymyxin B | | | |
| | MIC | MBC | MIC | MBC | MIC | MBC | MIC | MBC |
| Methicillin-resistant *Staphylococcus aureus* (ATCC 33591) | 800 | 800 | 800 | 800 | 100 | 100 | 8x | 8x |

| Testing Strain | MIC and MBC (μg/ml) | | | | | | Synergic Effect | |
|---|---|---|---|---|---|---|---|---|
| | Polymyxin B Alone | | t-2-Hexenal Alone | | t-2-Hexenal (½ MIC) +Polymyxin B | | | |
| | MIC | MBC | MIC | MBC | MIC | MBC | MIC | MBC |
| Methicillin-resistant *Staphylococcus aureus* (ATCC 33591) | 800 | 800 | 400 | 800 | 25 | 50 | 32x | 16x |

7.3 Synergic Effect of Indole with Polymixin B on *Candida albicans*

Tests were performed to determine the synergic effect of indole with polymyxin B on yeast fungi, in particular of *Candida albicans* (ATCC 10231). Results are given in Table 4.

TABLE 4

| Testing Strain | MIC and MBC (μg/ml) | | | | | | Synergic Effect | |
|---|---|---|---|---|---|---|---|---|
| | Polymyxin B Alone | | Indole Alone | | Indole (½ MIC) +Polymyxin B | | | |
| | MIC | MBC | MIC | MBC | MIC | MBC | MIC | MBC |
| *Candida albicans* (ATCC 10231) | 800 | 1600 | 400 | 800 | −200 | 400 | 4X | 4X |

7.4 Synergic Effect of Indole with Polymixin E on Gram-negative Bacteria

Tests were performed to determine the synergic effect of indole with polymyxin E on gram-negative bacteria of the strains *Escherichia coli* and *Pseudomonas aeruginosa* (ATCC 10536). Results are given in Table 5.

TABLE 5

| Testing Strain | MIC and MBC (μg/ml) | | | | | | Synergic Effect | |
|---|---|---|---|---|---|---|---|---|
| | Polymyxin E Alone | | Indole Alone | | Indole (½ MIC) +Polymyxin E | | | |
| | MIC | MBC | MIC | MBC | MIC | MBC | MIC | MBC |
| *Escherichia coli* (ATCC 10536) | 3.13 | 6.25 | 800 | 800 | 0.78 | 0.78 | 4X | 8X |

TABLE 5-continued

| Testing Strain | MIC and MBC (μg/ml) | | | | | | | | Synergic Effect |
|---|---|---|---|---|---|---|---|---|---|
| | Polymyxin E Alone | | Indole Alone | | Indole (½ MIC) +Polymyxin E | | | | |
| | MIC | MBC | MIC | MBC | MIC | MBC | MIC | MBC | |
| Pseudomonas aeruginosa (ATCC 10536) | 6.25 | 12.5 | 400 | 800 | 0.39 | 0.78 | 16X | 16X | |

7.5 Synergic Effect of Indole with Polymyxin E on Yeast

Tests were performed to determine the synergic effect of indole with polymyxin E on a range of quite different microbes, including the gram-negative bacteria *Escherichia coli* (ATCC 10536) and *Pseudomonas aeruginosa* (ATCC 10145), and the yeast *Candida albicans* (ATCC 10231). Results are given for *Candida albicans* in Table 6.

TABLE 6

| Testing Strain | MIC and MBC (μg/ml) | | | | | | | | Synergic Effect |
|---|---|---|---|---|---|---|---|---|---|
| | Polymyxin E Alone | | Indole Alone | | Indole (½ MIC) +Polymyxin B | | | | |
| | MIC | MBC | MIC | MBC | MIC | MBC | MIC | MBC | |
| Candida albicans (ATCC 10231) | 1600 | 1600 | 400 | 800 | 100 | 200 | >16X | >8X | |

8. Example: Synergic Effect of Anacardic Acid with Long-Chain Alcohols on *Staphylococcus aureus*

Testing was conducted to determine a synergic effect of anacardic acid with long chain n-alcohols (Undecanol, Dodecanol, Tridecanol) against methicillin-resistant *Staphylococcus aureus* (ATCC 33591). Results are given in Table 7.

TABLE 7

| Testing Strain | MIC (μg/ml) | | | Synergic Effect |
|---|---|---|---|---|
| | Undecanol Alone | Anacardic Acid (15:3) Alone | Anacardic Acid (15:3) (½ MIC) +Undecanol | |
| Methicillin-Resistant Staphylococcus aureus (ATCC 33591) | 50 | 6.25 | 12.5 | 4x |

TABLE 7-continued

| Dodecanol Alone | Anacardic Acid (15:3) Alone | Anacardic Acid (15:3) (½ MIC) +Dodecanol | |
|---|---|---|---|
| 80 | 6.25 | 10 | 8x |

| Tridecanol Alone | Anacardic Acid (15:3) Alone | Anacardic Acid (15:3) (½ MIC) +Tridecanol | |
|---|---|---|---|
| 50 | 6.25 | 25 | 2x |

9. Incorporation by Reference

All publications and patents mentioned herein are hereby incorporated by reference to the same extent as though each were individually so incorporated.

What is claimed:

1. A pharmaceutical composition comprising a polymyxin and a potentiator of antimicrobial activity wherein the potentiator is indole or 3-methylindole.

2. A method for preventing the growth of a microorganism selected from the group consisting of gram-negative bacteria, gram-positive bacteria and yeast comprising contacting said microorganism with a polymyxin and a potentiator of antimicrobial activity, wherein said potentiator is indole, 3-methylindole, or t-2-hexenal.

3. The method of claim 2 wherein the microorganism is a gram-negative bacterium.

4. The method of claim 3 wherein the bacterium is *E. coli* or *Pseudomonas aeruginosa*.

5. The method of claim 2 wherein the microorganism is a gram-positive bacterium.

6. The method of claim 5 wherein the bacterium is *Staphylococcus aureus*.

7. The method of claim 2 wherein the microorganism is a yeast.

8. The method of claim 7 wherein the yeast is *Candida albicans*.

9. A method for preventing the growth of a microorganism selected from the group consisting of methicillin-resistant *Staphylococcus aureus, E.coli, Pseudomonas aeruginosa* and yeast, comprising contacting the microorganism with a polymyxin and a potentiator of said growth prevention, wherein said potentiator is t-2-hexenal.

10. The method of claim 9, wherein the yeast is *Candida albicans*.

11. A method for preventing the growth of a microorganism selected from the group consisting of gram-negative bacteria, gram-positive bacteria and fungi, comprising contacting said microorganism with a polymyxin and a potentiator of antimicrobial activity, wherein said potentiator is indole or 3-methylindole.

* * * * *